(12) United States Patent
Kennedy

(10) Patent No.: US 8,801,718 B1
(45) Date of Patent: Aug. 12, 2014

(54) METHOD OF USING A TENDON TENSION DEVICE

(71) Applicant: James Woodfin Kennedy, Chattanooga, TN (US)

(72) Inventor: James Woodfin Kennedy, Chattanooga, TN (US)

( * ) Notice: Subject to any disclaimer, the term of this patent is extended or adjusted under 35 U.S.C. 154(b) by 0 days.

(21) Appl. No.: 13/948,221

(22) Filed: Jul. 23, 2013

Related U.S. Application Data

(62) Division of application No. 13/282,937, filed on Oct. 27, 2011.

(60) Provisional application No. 61/410,415, filed on Nov. 5, 2010.

(51) Int. Cl.
*A61F 2/46* (2006.01)
*A61F 2/08* (2006.01)

(52) U.S. Cl.
CPC .......................................... *A61F 2/08* (2013.01)
USPC ........................................ 606/86 R; 606/103

(58) Field of Classification Search
CPC ....... A61F 2/0805; A61F 2/0811; A61F 2/08; A61F 2002/0852; A61B 17/1714; A61B 17/1764
USPC ........... 606/277, 324, 147, 151, 157, 101, 99, 606/86 A, 86 B, 86 R; 81/467; 72/458, 479, 72/64–65; 140/123–124
See application file for complete search history.

(56) References Cited

U.S. PATENT DOCUMENTS

| 1,044,551 | A | * | 11/1912 | Lynch ........................ 140/123.5 |
| 5,632,748 | A | * | 5/1997 | Beck et al. ....................... 606/89 |
| 2002/0120275 | A1 | * | 8/2002 | Schmieding et al. ......... 606/104 |

FOREIGN PATENT DOCUMENTS

WO     WO2006014306 A1 *  2/2006  ............. A61B 17/58

* cited by examiner

*Primary Examiner* — David Bates
*Assistant Examiner* — Samuel Hanna
(74) *Attorney, Agent, or Firm* — Stephen J. Stark; Miller & Martin PLLC

(57) ABSTRACT

A method of using a tenolysis tool with a handle connected to at least two extension members which could be tines of a fork separated by a gap. Between the extension members and at least a portion of the handle may be a torque device selected from the group of a torque release and a torque indicator. By placing a tendon in the gap between the tines, the tool can be twisted so that the tendon is stretched under a torque.

6 Claims, 1 Drawing Sheet

METHOD OF USING A TENDON TENSION DEVICE

CLAIM OF PRIORITY

This application is a divisional application of U.S. application Ser. No. 13/282,937 filed on Oct. 27, 2011 which claims the benefit of U.S. Provisional Patent Application No. 61/410,415 filed Nov. 5, 2010.

FIELD OF THE INVENTION

The present invention relates to a tension device and method of its use, and more specifically, to a tool and method of its use for use in performing a tenolysis in a presently preferred embodiment of the present invention.

DESCRIPTION OF RELATED ART

Flexor tenolysis is a procedure used to remove adhesions from tendons and is often designed to improve active digital flexion. Despite attempts to develop surgical and rehabilitation techniques to maximize flexor tendon function following surgical repair, post-operative tendon adhesions traditionally remain a problem. In these situations, flexor tenolysis of non-gliding adhesions have been found to markedly improve the function of digit. In more laymen's terms, the fingers become stiff following some type of injury. Moving parts of the fingers are effectively glued together by scar tissue and if movement cannot be recovered through therapy and time, in some certain applications, tenolysis has been found helpful. Tenolysis can be performed on many tendons through the body, and is not just limited to digit tendons.

Tendon hooks are well known in the art. In performing a tenolysis, surgeons typically utilize a tendon hook which looks similar to how it sounds, but the end of the hook end is typically blunt. Specifically, the hook is utilized to "catch" the tendon and then pulled it up and out of the anatomic plane of normal operation to effectively pull the tendon free from the adhesions.

Unfortunately, when a tendon is pulled out of its normal plane of operation in a direction that it is not designed to operate in relative to the human body during normal operation, it may damage the pulleys that the tendon slides through. This can aggravate problems with the tendon and/or create additional problems for the patient.

Accordingly, a method and device is believed to be necessary in order to attempt to minimize the out of plane movement of tendons during tenolysis and/or provide a more effective means of treating stiff or adhered tendons to provide an improved method of tenolysis and the tools to accomplish the same.

SUMMARY OF THE INVENTION

It is the object of a presently preferred embodiment of the present invention to provide an improved tenolysis tool and method of its use.

It is another object of a presently preferred embodiment of the present invention to provide a tenolysis tool and method of its use which may assist in pulling a tendon in approximately opposing directions.

It is another object of the present invention to provide a method and apparatus which may twist the tendon at least in some embodiments.

It is another object of at least some embodiments of the present invention to attempt to reduce possibility of damage to pulleys by which tendons operate.

It is another object of at least some embodiments of the present invention to increase the surface area acting on tendons during tenolysis procedures in an effort to minimize point of contact damage to tendons during tenolysis.

Accordingly, in accordance with a presently preferred embodiment of the present invention, a tool has at least two extending members in the form of tines separated by a gap which receives a portion of a tendon in the gap. The operator can twist the tool whereby the tines contact the tendon and opposing portions of the tines can pull the tendon in two different directions.

This device has the ability to twist and/or stretch the tendon without significantly pulling the tendon out of its normal anatomic plane. This procedure is believed to reduce a likelihood of damage to the pulleys through which and on which the tendon normally operates.

Furthermore, the force which can be applied to the tendon is believed to be increased over prior art devices in that since there are two tines, the tool effectively doubles the contact area acting on the tendon during a tenolysis procedure. This effect is believed to decrease a potential likelihood damage to tendon surfaces and potentially promote better function and faster recoveries for a given force application. Additionally, providing more force on a tendon than previously provided may now be a possibility which may address more scar tissue which may potentially be freed from the tendon at least in some embodiments in prior art techniques due to increased surface area acting on the tendon and/or acting at least substantially in the place of normal tendon operation.

A torque measurement device and/or a torque release can be incorporated into the handle or otherwise to allow and/or indicate an exertion force applied to the tendon in an effort to prevent rupture of the tendon. This device is believed to be useful in applying tension to tendon grafts such as those used in ACL reconstruction, other tenolysis operations, or possibly other application. Tools can be gauged so that if a shaft torques to 90°, it can represent a calculated force of tension being applied to the tendon at least for some embodiments. The preferred tools can be injection molded or made from other appropriate materials and methods. Injection molded tools are believed to be particularly attractive in that a disposable product can be provided.

Although tenolysis is a presently preferred procedure for utilizing the presently preferred tool and its preferred methods are utilized, other applications and/or other embodiments may be discovered but not yet known by the applicant.

BRIEF DESCRIPTION OF THE DRAWINGS

The particular features and advantages of the invention as well as other objects will become apparent from the following description taken in connection with the accompanying drawings in which.

DETAILED DESCRIPTION OF THE INVENTION

Figure 1:
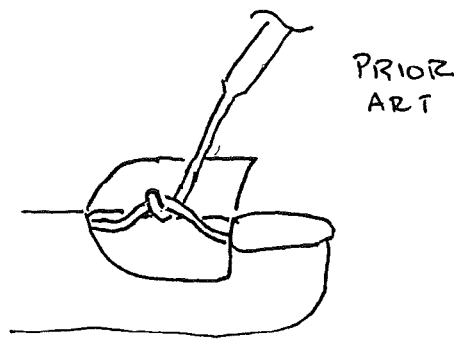
FIG. 1 is a perspective view of a tenolysis procedure utilizing a prior art tendon hook acting on a tendon in a finger.

FIG. 1 is a prior art method of performing tenolysis. A prior art hook with a blunt end is traditionally utilized to pull tendons up and out of the anatomic plane of the tendon to attempt to free the tendon from adhesions.

Figure 2:
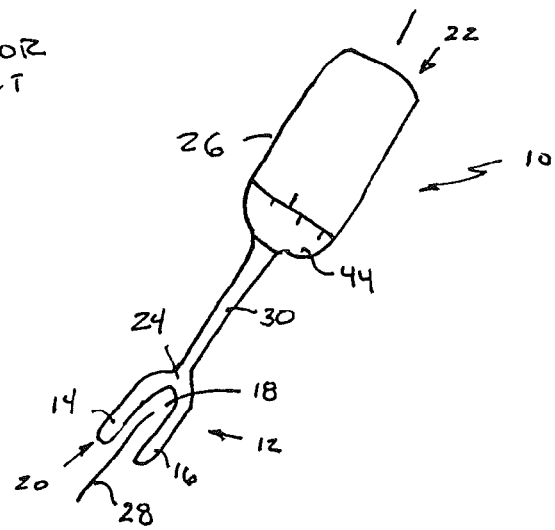
FIG. 2 is a top perspective view of a tool in the presently preferred embodiment of the present invention.

FIG. 2 shows a tool 10 of the presently preferred embodiment of the present invention. Tool 10 is shown in operation in FIGS. 3-6. Tool 10 has an operator 12 comprised of a fork in the presently preferred embodiment which has first and second tines 14,16 separated by gap 18 disposed towards an end 20 such as distal end. Proceeding towards proximal end 22 of tool 10, the tines 14,16 may meet in a yoke 24 or otherwise connect to handle 26.

Although a handle 26 is shown oriented on or about on the same orientation axis 28 as an axis extending through gap 18, other dispositions of handle 26 relative to tines 14,16 and/or gap could be provided in other embodiments. Specifically, extension 30 or other portion could be bent, angled or otherwise provided in other embodiments.

Figure 3:
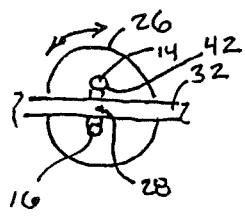
FIG. 3 is a front view of the tool shown in FIG. 2 acting on a tendon.
Figure 4:
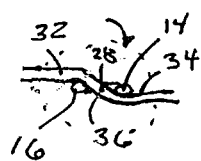
FIG. 4-6 are front views of a portion of the tools shown in FIGS. 2 and 3 performing a presently preferred embodiment of a method according to the present invention.
Figure 5:
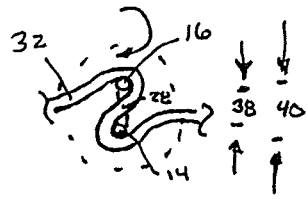
Figure 6:
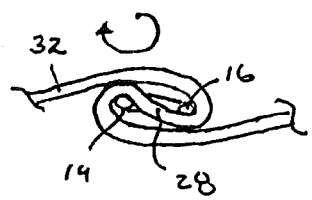

FIG. 3 shows that tines 14,16 may be rotated about axis 28 such as by rotating handle 26. In other embodiments, axis 28 may only make sense relative to tines 14,16 instead of to the entire tool as illustrated and as would be understood by those of ordinary skill in the art such as has been described above. Upon affecting rotation of tine 14 relative to the tine 16, such as for a total rotation of 90° as shown in FIG. 4, tendon 32 begins to be stretched as tine 14 pushes down on an upper surface 34 of tendon 32 while tine 16 pushes upward on a lower surface 36 of tendon 32. Rotation in the opposite direction is also possible as would be understood by those of ordinary skill in the art. By continuing to twist in the same direction as is shown in FIG. 5 such as another 90° of rotation, the amount of stretch on tendon 32 now exceeds a width 38 distance of the gap 18, and furthermore exceeds the width 40 which is the width of the gap 18 in combination with the width of tines 14,16 which could be diameters or could be other dimensions depending on the construction of tines 14,16 as illustrated in FIG. 5. By continuing to twist yet another 90°, the total amount of stretch can be greater than two times the width 40 as shown in FIG. 6.

By selecting the configuration of a specific tool 10, the widths 38,40 can be selected and/or predetermined for a particular procedure. Tines 14,16 may have multiple widths 38,40 along their lengths in other embodiments. Additionally, by having two tines 14,16, an effective doubling of the amount of surface area 42 can be placed in contact with tendon 32 during the procedure. This is believed to decrease potential damage that could be done to the tendon surfaces and/or increase an amount of tension applied to the tendon 32 during tenolysis.

Upper surface 34 and lower surface 36 are contacted by tines 14,16. This is believed to provide fast recovery and better function of the tendon 32 after healing from the procedure. Additionally, a torque device 44 such as an automatic torque device shown in FIG. 2 could be provided as with and/or a part of or in conjunction with handle 26 or otherwise provided with tool 10 so that as handle 26 or other portion is twisted thereby applying rotation to tines 14,16, upon reaching a predetermined limit and/or adjustable limit, the torque device 44 may release to prevent further stretch upon reaching a maximum amount of force or torque exerted upon the tendon 32 during the tenolysis procedure for at least some embodiments. This is believed to assist preventing tendon rupture or other complications. Tool 10 may be useful in tension of tendon grafts used in ACL reconstruction or other procedures.

Additionally, the torque device 44 in some embodiments could identify a force and/or tension being applied to the tendon and could be gauged so that a shaft twist of up to 90° relative to the handle 26 may gauge a particular amount of force or tension on the tendon 32.

Handle 26 is illustrated as a screwdriver type handle. Other handles as known in the art can be utilized. Tendon 32 is shown flexibly wrapped about tines 14,16 in FIG. 6 and it is possible that further rotation can occur in still other embodiments and methods. Other tine configurations as are known in the art could also be employed with curved tines, non-parallel tines and other configurations which might assist in initially placing and/or retaining the gap 18 about tendon 32 in order to begin initiation of applying tension and/or maintaining tension as shown in FIGS. 3-6.

It is important to observe and recognize that in FIG. 1 the tendon illustrated is pulled out of the anatomical plane and/or axis or operation as shown which potentially could damage the pulley that the tension slides through (not shown). By performing the preferred method as shown in FIGS. 2-6, with tool 10 as shown in FIGS. 2-6, it is understood that the plane of operation of the tendon during procedure can be at least essentially maintained. At most, the tendon 32 is pulled from its normal operational position at the tool 10 by roughly half of width 40 or over up to width 40 on one side of tendon 32 with the other side being stretched along its normal axis of operation.

Depending on the configuration of the tines 14,16 essentially the same directions of operation of the tendon 32 can be maintained without significant alternations of the direction of operation of the tendon 32 during the tenolysis procedure. It is believed that there is significantly less likelihood of damage to the pulleys is likely to occur utilizing the applicant's presently preferred tool and method of operation.

Numerous alterations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

1. A method of using a tendon tension device for performing a tenolysis procedure comprising:
 (a) providing a device extending along a longitudinal axis, the device having a handle, at least two extending members connected to the handle, said extending members having respective tendon contacting surfaces separated by a gap; and
 a torque device selected from the group of one of a torque release and a torque measurement device provided intermediate a portion of the handle and the at least two extending members, and
 (b) placing a tendon of a body having digits in the gap and twisting the two extending members about the longitudinal axis of the device so that the two extending members apply a torque to the tendon, with the torque device providing at least one of (a) an indication of an amount of torque applied, and (b) a release of torque on the tendon upon reaching a predetermined amount of torque;
  wherein the two extending members extend from a yoke, and the yoke is connected to the handle and the twisting step is the tenolysis procedure;
  wherein the two extending members are tines of a fork extending cantileveredly from the yoke;
  wherein a width is defined as a maximum distance between the tines; and wherein when the two extending members are twisted 90 degrees about the longitudinal axis of the device, the tendon is stretched by a distance measuring about the width.

2. The method of claim 1 wherein the torque device is intermediate the yoke and the portion of the handle.

3. The method of claim 1 wherein the tendon is pulled outside of a normal operating axis of the tendon no more than the width while applying torque to the tendon.

4. The method of claim 3 wherein the tendon is pulled outside of the normal operating axis of the tendon no more than about half of the width while applying torque to the tendon.

5. The method of claim 1 wherein when the two extending members are twisted 180 degrees about the longitudinal axis of the device, the tendon is stretched by a distance measuring about two times the width.

6. The method of claim 1 wherein the handle is disposed along the longitudinal axis and the longitudinal axis is parallel to the extending members.

* * * * *